United States Patent [19]

Wohlstadter

[11] Patent Number: 5,922,584
[45] Date of Patent: *Jul. 13, 1999

[54] METHOD FOR PROMOTING ENZYME DIVERSITY

[76] Inventor: Jacob N. Wohlstadter, 19 Everett St., #34, Cambridge, Mass. 02138

[*] Notice: This patent is subject to a terminal disclaimer.

[21] Appl. No.: 08/671,906

[22] Filed: Jun. 6, 1996

Related U.S. Application Data

[63] Continuation-in-part of application No. 08/476,135, Jun. 7, 1995, and a continuation-in-part of application No. 08/505,528, Jun. 7, 1995.

[51] Int. Cl.$^6$ ..................................................... C12N 9/00
[52] U.S. Cl. .......................................... 435/188.5; 435/7.6
[58] Field of Search .................................... 435/7.6, 188.5

[56] References Cited

U.S. PATENT DOCUMENTS

| | | | |
|---|---|---|---|
| 4,792,446 | 12/1988 | Kim et al. | 424/85.8 |
| 4,963,355 | 10/1990 | Kim et al. | 424/85.8 |
| 5,037,750 | 8/1991 | Schochetman et al. | 435/183 |
| 5,156,965 | 10/1992 | Schochetman et al. | 435/188.5 |
| 5,318,897 | 6/1994 | Paul | 435/68.1 |
| 5,401,641 | 3/1995 | Kim et al. | 435/41 |

FOREIGN PATENT DOCUMENTS

| | | |
|---|---|---|
| WO 91/10741 | 7/1991 | WIPO. |
| WO 92/03918 | 3/1992 | WIPO. |
| WO 93/19170 | 9/1993 | WIPO. |
| WO 94/25585 | 11/1994 | WIPO. |
| WO 94/25586 | 11/1994 | WIPO. |

OTHER PUBLICATIONS

Green, N. S., et al. (1998) BioEsssays 20, 227–234.
Wedemayer, G. J., et al. (1997) J. Mol. Biol. 268, 390–400.
Sun, M., et al. (1997) J. Mol. Biol. 271, 374–365.
DeSutter, K., et al. (1994) Mol. Immun. 31(4), 261–267.
Rosenthal, D., et al. (1994) Biochem. Biophys. Res. Comm. 202(2), 880–887.
Titmas et al., "Aspects of Antibody–Catalyzed Primary Amide Hydrolysis," *Applied Biochemistry and Biotechnology*, 1994, vol. 47, pp. 277–290.
Suzuki, H. "Recent Advances in Abzyme Studies," *J. Biochem.*, 1994, vol. 115, No. 4, pp. 623–628.
Smiley et al., "Selection of catalytic antibodies for a biosynthetic reaction from a combinatorial cDNA library by complementation of an auxotrophic Escherichi coli: Antibodies for orotate decarboxylation," *Proc. Natl. Acad. Sci. USA*, 1994, vol. 91, No. 18, pp. 8319–8323.
Janda, et al., "Direct selection for a catalytic mechanism from combinational antibody libraries," *Proc. Natl. Acad. Sci. USA*, 1994, vol. 91, No. 7, pp. 2532–2536.
Taylor, et al., "A transgenic mouse that expresses a diversity of human sequence heavy and light chain immunoglobulins," *Nucleic Acids Research*, 1992, vol. 20, No. 23, 6287–6295.
Sarvetnick, et al., "Increasing the chemical potential of the germ–line antibody repertoire," *Proc. Natl. Acad. Sci. USA*, 1993, vol. 90, No. 9, pp. 4008–4011.
Thorn, et al., "Large rate accelerations in antibody catalysis by strategic use of heptenic charge," *Nature*, 1995, vol. 373, no. 6511, pp. 228–230.
Lonberg, N., et al., "Antigen–specific human antibodies from mice comprising four distinct genetic modification," *Nature*, 1994, vol. 368, pp. 856–859.
Green, L.L., et al., "Antigen–specific human monoclonal antibodies from mice engineered with human lg heavy and light chain YACs," *Nature Genetics*, 1994, vol. 7, pp. 13–21.
Oliphant, A.R., et al., "An efficient method for generating proteins with altered enzymatic properties: Application to β–lactamase," *Proc. Natl. Acad. Sci. USA*, 1989, vol. 86, pp. 9094–9098.

*Primary Examiner*—Charles L. Patterson, Jr.
*Attorney, Agent, or Firm*—Whitman, Breed Abbott & Morgan, LLP

[57] ABSTRACT

The invention is directed to a method for generating novel catalysts; particularly high turnover rate enzymes or biocatalysts. Functional catalytic units may be integrated into the germline composition of an animal in order to generate such novel catalysts.

48 Claims, 9 Drawing Sheets

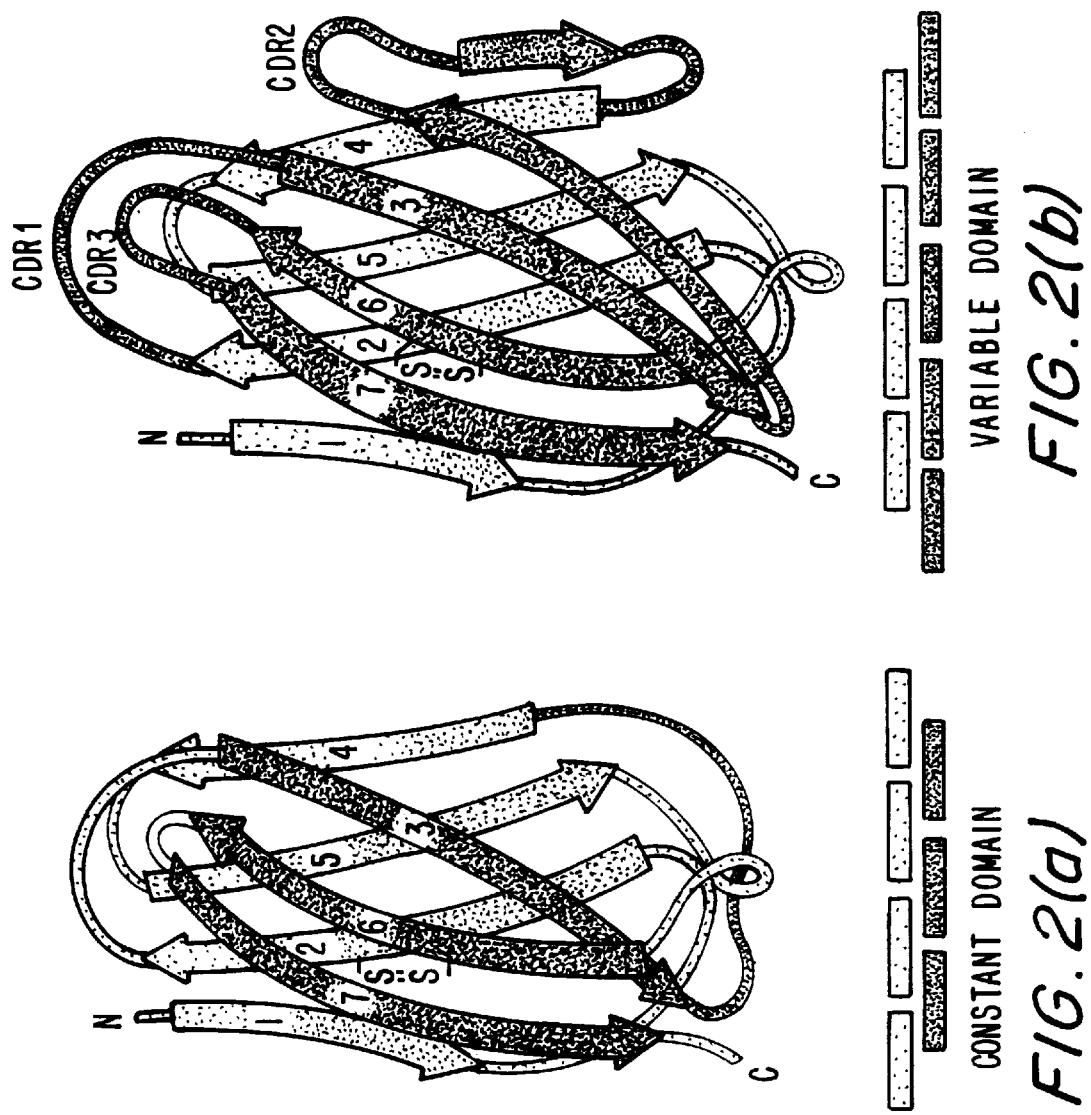

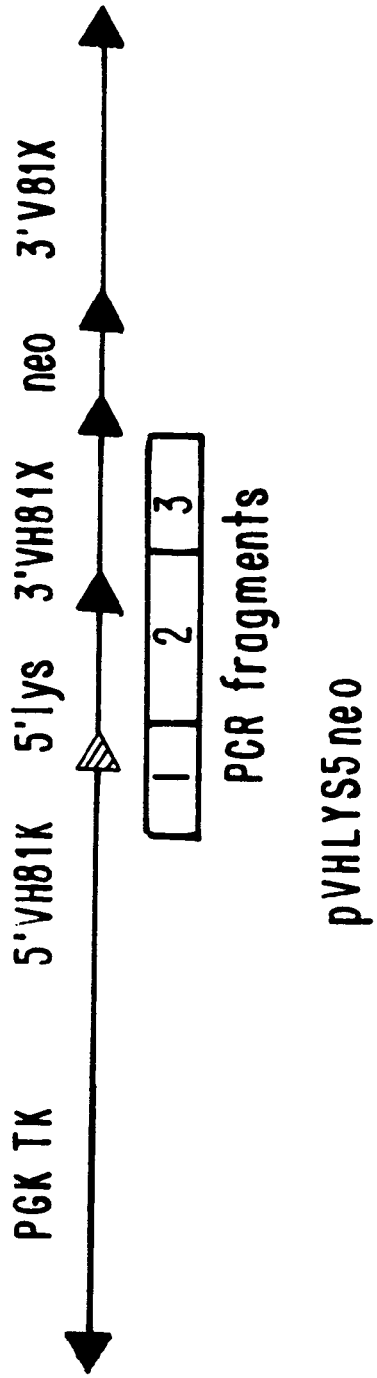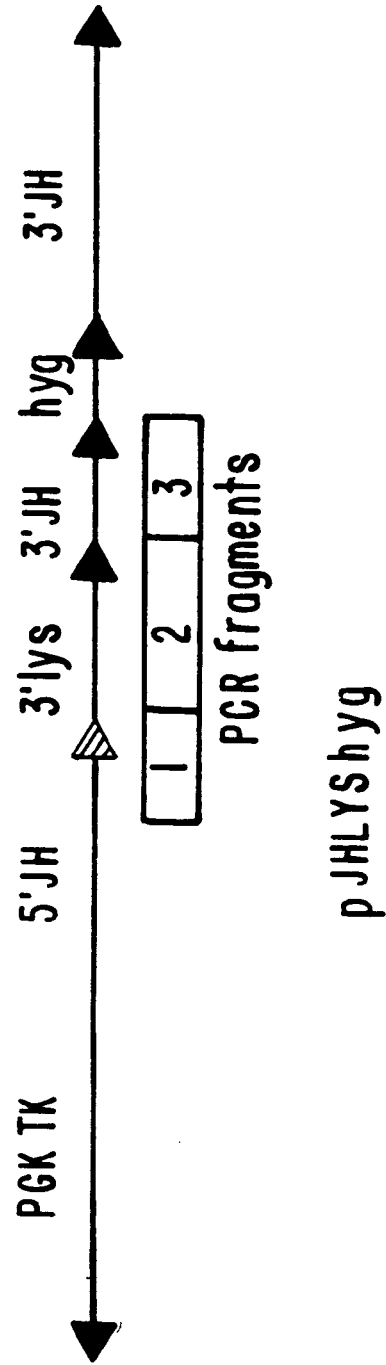

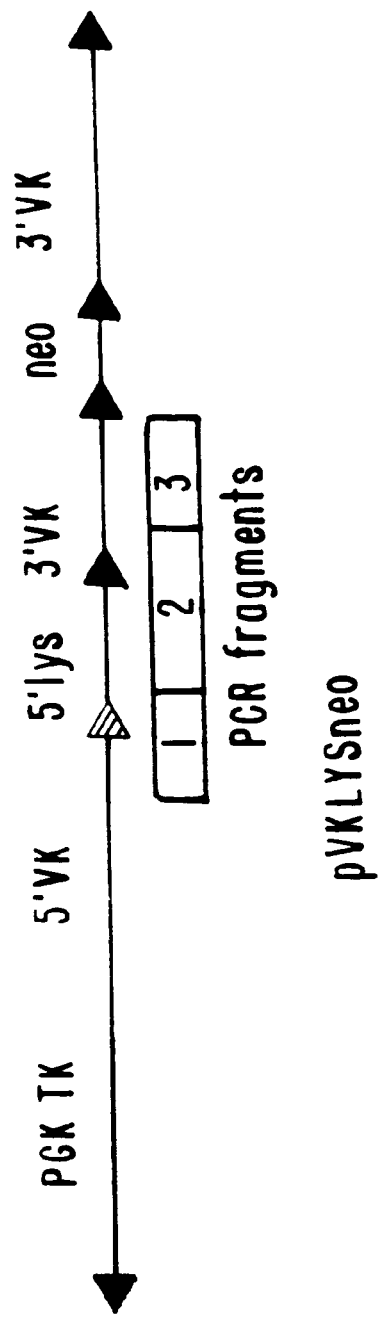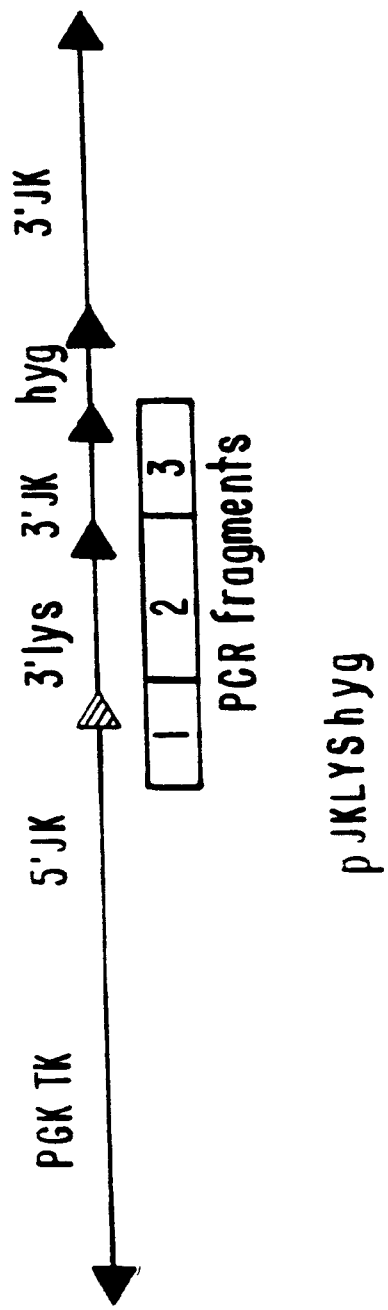

METHOD FOR PROMOTING ENZYME DIVERSITY

CROSS-REFERENCES TO RELATED APPLICATIONS

This application is a continuation-in-part of prior copending U.S. patent application Ser. No. 08/476,135 filed Jun. 7, 1995 and Ser. No. 08/505,528 filed Jun. 7, 1995.

FIELD OF THE INVENTION

The present invention relates broadly to methods for creating novel catalysts, particularly high turnover rate enzymes or biocatalysts, using animals of altered germline sequence. More particularly, the invention relates to methods for promoting rapid evolution or diversification of the specificity regions of an enzyme. The method can be used to produce antibodies with catalytic activity by encoding a functional catalytic unit or a substantial portion thereof into a germline antibody gene locus. And even more particularly, the invention relates to the placement and segmentation of the enzymatic sequences within the antibody gene loci.

BACKGROUND OF THE INVENTION

Over the last decade, research has been devoted to the production of useful antibodies with catalytic activity. Such antibodies are commonly known as catalytic antibodies or Abzymes. Catalytic antibodies with enhanced turnover rates as compared with uncatalyzed reaction rates have been reported by a number of research groups. (see Suzuki et al., "Recent advances in abzyme studies," 115(4) Journal of Biochemistry 623–8(1994) which is incorporated herein by reference, Titmas et al., "Aspects of antibody catalyzed primary amide hydrolysis, 47(2–3) Applied Biochemistry & Biotechnology 277–90 (1994) which is incorporated herein by reference). See also U.S. Pat. Nos. 5,037,750 and 5,156,965 to Schochetman and Massey, which are incorporated herein by reference, which teach a method for increasing the rate of chemical reactions involving the conversion of at least one reactant to at least one product.

In some instances, large rate enhancements over uncatalyzed reaction rates have been achieved (see Thorn et al., "Large rate accelerations in antibody catalysis by strategic use of haptenic charge," 373 Nature 228–30(1995) which is incorporated herein by reference). Thus far, however, a generic means has not been found to employ traditional laboratory techniques to produce highly efficient specific catalysis with catalytic antibodies.

The traditional laboratory techniques for producing a catalytic antibody is through the use of transition state analogs (TSA) (see U.S. Pat. No. 4,792,446 to Kim and Kallenbach, which is incorporated herein by reference). The TSA is a stable mimic of the unstable intermediate conformation of a reactant molecule. Animals are immunized with TSA's in the hopes of producing antibodies which by virtue of their ability to bind the TSA's may have the ability to stabilize the transition state of the reactant and to catalyze the formation of the desired product. Hybridomas are then screened by assaying for the desired catalytic activity.

The overwhelming problem that has plagued catalytic antibody development in the vast majority of cases is the lack of high turnover rates. Except in rare instances, catalytic antibodies are orders of magnitude slower catalysts than similar enzymes found in nature.

Recently, however, selection methods have been used to produce catalytic antibodies (see Smiley et al., "Selection of catalytic antibodies for a biosynthetic reaction from a combinatorial cDNA library by complementation of an auxtrophic *Escherichia coli*: antibodies for orotate decarboxylation," 91(18) Proceedings of the National Academy of Sciences of the United States of America 8319–23 (1994), which is incorporated herein by reference; Janda et al., "Direct selection for a catalytic mechanism from combinatorial anyiboby libraries," 91(7) Proceedings of the National Academy of Sciences of the United States of America 2532–6), which is incorporated herein by reference. Such methods use selection pressure to isolate antibodies with desired properties instead of the more laborious screening techniques. For example, a catalytic antibody which catalyzes the formation of a cellular growth factor may be selected for in a cell auxotrophic for such growth factor.

Advances in molecular and cell biology have given researchers the ability to alter the germ line genetic constitution of a variety of animals. Pieces of genes, whole genes, and/or chromosomal regions may be selectively deleted or added. Recently these transgenic/knock-out techniques have been used to produce human proteins in other species. In particular, it has been possible to produce human antibodies in rodents(see Green et al.,"Antigen-specific human monoclonal antibodies from mice engineered with human Ig heavy and light chain YAC's"7(1) Nature Genetics 13–21 (1994), which is incorporated herein by reference; Lonberg et al., "Antigen-specific human antibodies from mice comprising four distinct genetic modifications," 368(6474) Nature 856–9(1994), which is incorporated herein by reference; Taylor et al.,"A transgenic mouse that expresses a diversity of human sequence heavy and light chain immunoglobulins," 20–23 Nucleic Acids Research 6287–95 (1992), which is incorporated herein by reference). International applications WO 91/10741; WO 94/25585; and WO 92/03918 also discuss diversity of human sequence heavy and light chain immunoglobulins and are incorporated herein by reference. The ability to produce human antibodies in rodents allows for the controlled production of therapeutic antibodies of low immunogenicity.

In an extension of the traditional method of the catalytic antibody technique for increasing antibody binding affinity to enzymatically relevant conformations and co-factors, transgenic animals have been utilized to enhance the germline antibody metal ion binding capability. Metal ions are used as co-factors for various enzymes and transgenic mice were produced to more effectively bind metal cations (see Sarvetnick et al., 1993, "Increasing the chemical potential of the germ-line antibody repertoire." 90(9) Proceedings of the National Academy of Sciences of the United States of America 4008–11, which is incorporated herein by reference; WO 94/25586, which is incorporated herein by reference).

In the present invention, rather than promoting binding, as has been done in past studies, applicant proposes integrating functional catalytic units into the germline composition of an animal such that the sequences encoding the specificity determining regions of the enzymatic activity are diversified in an analogous fashion to immunoglobulin variable regions. Such an approach solves the problem of low turnover rate or low catalytic activity.

SUMMARY OF THE INVENTION

Accordingly, the present invention provides a novel method for utilizing transgenic/knock-out germline altering techniques to implant sequences encoding functional catalytic domains and/or structures in the germline antibody sequence of an animal.

In accordance with one aspect of the present invention, such sequences encoding functional catalytic domains and/or structures are sequences of known enzymes with the desired catalytic function (e.g., hydrolysis of a peptide bond) but with specificity different from the desired catalytic antibody.

In still another aspect of the present invention, the sequences encoding the specificity regions of the implanted functional enzyme are inserted into the germline of the animal so as to correspond to the CDR regions of the antibody so as to promote rapid evolution/diversification of the specificity regions of the enzyme. The invention is also in the transgenic implantation of functional catalytic units or enzymes in other (non-antibody) chromosomal regions of high mutation rate (e.g., T cell receptor gene sequences).

And yet another aspect of the present invention, the method provides for a varying array of chimeric antibody/enzyme structures. The placement and segmentation of the enzymatic sequence allows for the production of a multitude of antibody/enzyme structures.

BRIEF DESCRIPTION OF THE DRAWINGS

FIG. 2 illustrates a comparison of the structures of the constant and variable domains of immunogobulins, β strands labeled 1–7 have the same topology and similar structures. There are two extra β strands, in the variable domain. The loop between these strands contain the hypervariable region CDR2. The remaining CDR regions are at the same end of the barrel in the loops connecting β strands 2 and 43 and strands 6 and 7. A disulfide bond bridges strand 2 in one sheet with strand 6 in the other sheet in both the constant and the variable domains.

FIG. 5 is a diagram of preparation of (a) pVHLYSneo and (b) pJHLYShyg.

FIG. 6 is a diagram of preparation of (a) pVKLYSneo and (b) pJKLYShyg.

DETAILED DESCRIPTION OF THE INVENTION

Figure 1:
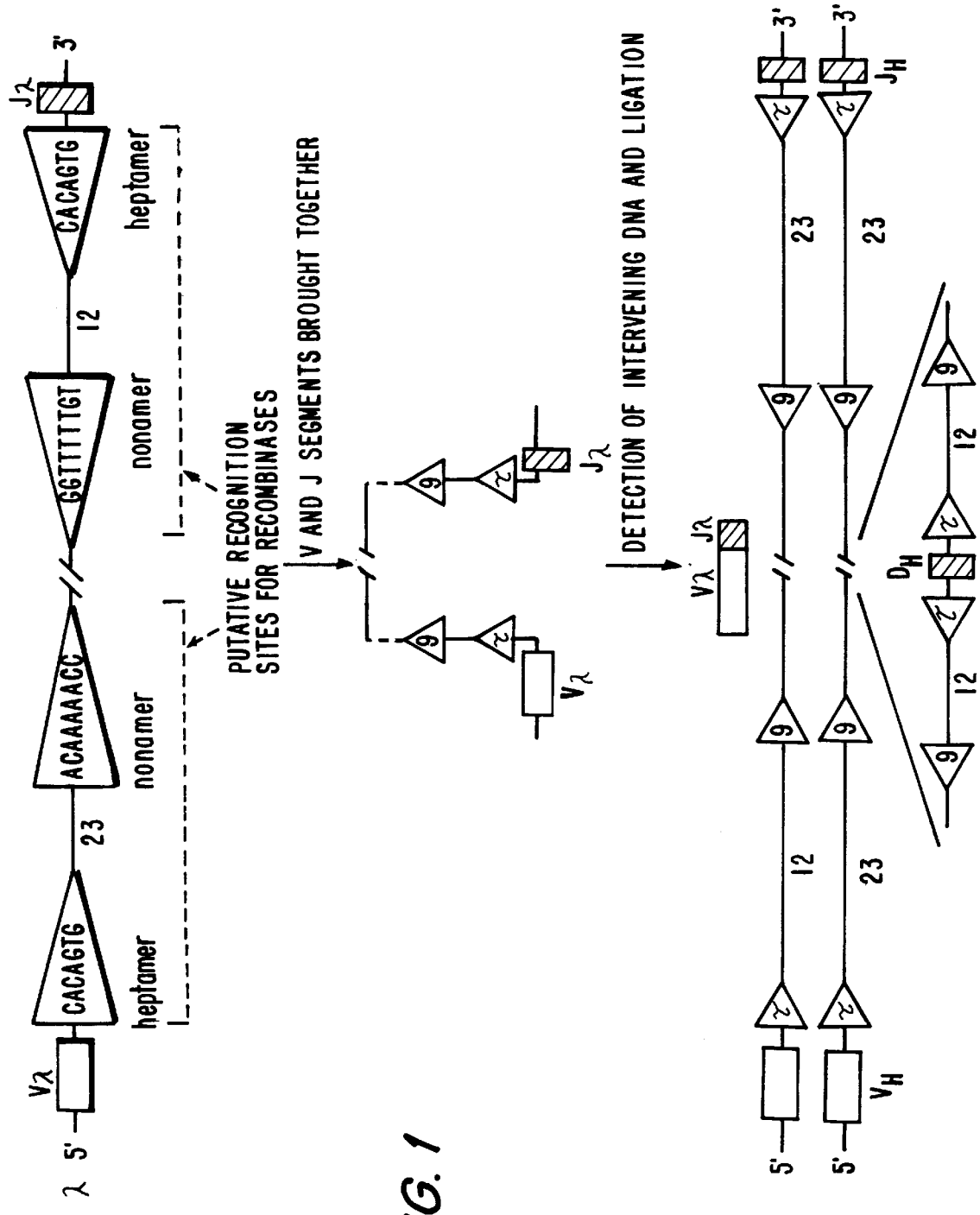
FIG. 1 shows a "DNA recognition sequences for recombinases that mediate Ig gene rearrangement. Conserved heptamer (7 bp) and nonamer (9 bp) sequences, separated by 12 or 23 base pair spacers, are located adjacent to V and J exons or V, D and J exons (in the H chain locus). Recombinases presumably recognize these regions and bring the exons together, forming loops of non-coding intervening DNA that are excised and the exons are joined. Alternatively, the exons can be joined by a process of inversion, followed by excision and ligation." 302 Nature 575(1983).

The following definitions are necessary for a proper understanding of the invention:

A catalytic engine is a functional catalytic unit capable of altering the rate of a reaction.

An evolutionary starting point is defined as a sequence (or protein encoded by said sequence) which encodes or has a desired property or is closely related to a sequence or protein with such property (e.g., catalytic activity).

As disclosed in WO 93/19170 to Wohlstadter, which is incorporated herein by reference, evolutionary starting points may be utilized to produce high turnover rate enzymes and/or other biocatalysts (e.g., ribozymes). In a broad sense enzymes and/or other biocatalysts may be considered to have two functionalities: the catalytic center which drives catalysis (catalytic engine) and the surrounding specificity regions which determine the substrate or reactant selectivity of the enzyme. Empirically, it has been found that functional catalytic domains or catalytic engines are common to enzymes of different specificity (see Branden et al., "Introduction to protein Structure," Garland Publishing (1991), which is incorporated herein by reference). This empirical data suggests that it is more efficient to maintain a functional catalytic domain or catalytic engine and evolve the specificity domains to create enzymes for new substrates than to evolve different catalytic functional units. Efficient biocatalysts require precise structural orientation of specific chemical moieties and often require complex serial temporal and spatial interaction with the reactant substrate (see Walsh, "Enzymatic Reaction Mechanisms," Freeman and Co., (1979), which is incorporated herein by reference). Simply binding to a specific molecular structure may be carried out with a variety of different molecules. This is best exemplified by antibodies. Many, substantially different antibody sequence/structures are capable of high affinity binding to the same antigen epitope. Further empirical evidence suggests that the stringent complex requirements needed to create a functional catalytic unit drastically restricts the number of chemical/structural conformations which are capable of carrying out catalysis whereas many different chemical/structural conformations may confer substantially similar binding affinity. For example, different proteins evolve substantially similar functional catalytic mechanisms. Even though such enzymes primary amino acid sequence are unrelated they convergently evolve the same catalytic mechanism (see Brandem). The evolutionary data indicates that to create a biocatalyst of new specificity it is evolutionarily more efficient to utilize an existing functional catalytic unit and evolve the specificity determining regions to achieve the desired substrate selectivity since only a relatively more restricted set of chemical/structural conformations are capable of forming a high efficiency catalytic unit. The current invention is in the increased efficiency of creating antibodies with catalytic activity by altering the germline antibody sequence of an animal to encode a functional catalytic unit or substantially all of a functional catalytic unit or enzyme.

A variety of different transition state analogs have been synthesized and used to immunize laboratory animals. TSA's and other immunogens of varying structures and charge have been utilized to elicit antibodies with catalytic activity with varying shape complementary structures and charge complimentary structures (for example, see Suzuki; Thorn; U.S. Pat. Nos. 4,792,446; 4,963,355; 5,156,965; 5,401,641; 5,318,897; which are incorporated herein by reference). TSA's may also be produced with extended structures to more fully mimic the structure of the desired substrate to increase selectivity. Additionally, immunization may be carried out using suicide substrate inhibitors (substrates which covalently bind to functional catalytic domains). A variety of antigens may be utilized in the present invention. Depending on the desired degree of selectivity, antigens of more exact and/or extensive similarity to the desired substrate may be used.

In some instances substantially all of a substrate may be utilized with only minor alterations or in other cases the substrate itself may be utilized. In a preferred embodiment of the invention enzyme inhibitors and or suicide substrates are used as antigens or components of antigens. In a particularly preferred embodiment of the invention enzyme inhibitors and or suicide substrates are integrated into the substrate or an analog thereof at the desired site of catalytic action on the substrate.

In the last several years advances in transgenic/knockout germline alteration have allowed the production of animals with varied properties. A variety of different groups have been able to alter the germline of antibody genes so as to produce human antibodies in other species. As is known by one skilled in the art, new genes and/or sequences may be introduced into an animal's germline and/or endogenous genes and/or sequences may be inactivated, disrupted, and/or deleted. In the current invention, such germline altering techniques are utilized to insert a functional enzyme sequence so as to create a chimeric antibody enzyme molecule such that the enzyme portion of the chimeric protein undergoes immunological evolution and selection generating antibodies with the desired enzymatic activity. In a preferred embodiment of the invention both the antibody sequences and the enzyme sequences are human sequences so as to limit the potential immunogenicity of the resulting catalytic antibody. In one embodiment, the use of yeast artificial chromosomes can be employed.

Antibodies are composed of several immunoglobulin domains which are covalently attached into the commonly known 'Y shaped' structure of two heavy chains and two light chains. Each heavy chain and each light chain contain one variable immunoglobulin domain and the remaining immunoglobulin domains are constant domains. Although slightly different in structure both variable and constant domains have anti-parallel β barrel tertiary structures (see FIG. 1). The loops connecting beta strands in the variable domains termed CDR1, CDR2 and CDR3 (Complimentary Determining Regions 1, 2 and 3) are found to vary widely between antibodies and confer antibody specificity. Antibody diversity is generated by a variety of means. For example, diversity may be generated by (1) multiple different germline genes (2) combinatorial diversity (3) junctional diversity including (a) imprecise DNA rearrangement and (b) N region diversification (4) varying combinations of heavy and light chain proteins and (5) somatic mutation (see Abbas et al., "Cellular and Molecular Immunology Second Edition," Saunders Co., (1994); Paul, "Fundamental Immunology Third Edition," Raven press (1993), which is incorporated herein by reference). Through proper insertion of the enzyme or functional catalytic unit within the germline such diversification mechanisms are imposed on the enzymatic portion of the antibody enzyme protein. For example, the V, D, and J regions of an antibody may be replaced with sequences from a known human enzyme. The intronic configuration of the antibody gene locus is maintained to foster extensive diversification. For example, repetitive sequences (nanomer and heptamer) as well as intronic spacing is maintained (see FIG. 1).

Figure 3A:
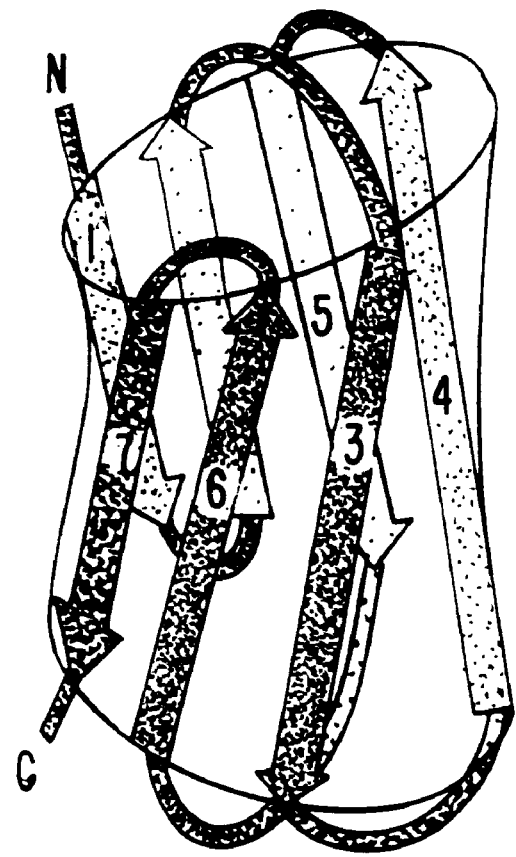
FIG. 3 is a view of the constant domains of immunoglobulins folded into a compressed antiparallel β barrel built up from one three-stranded β sheet packed against a four stranded sheet (a). The topological diagrams (b) show the connected Greek key motifs of this fold.
Figure 3B:
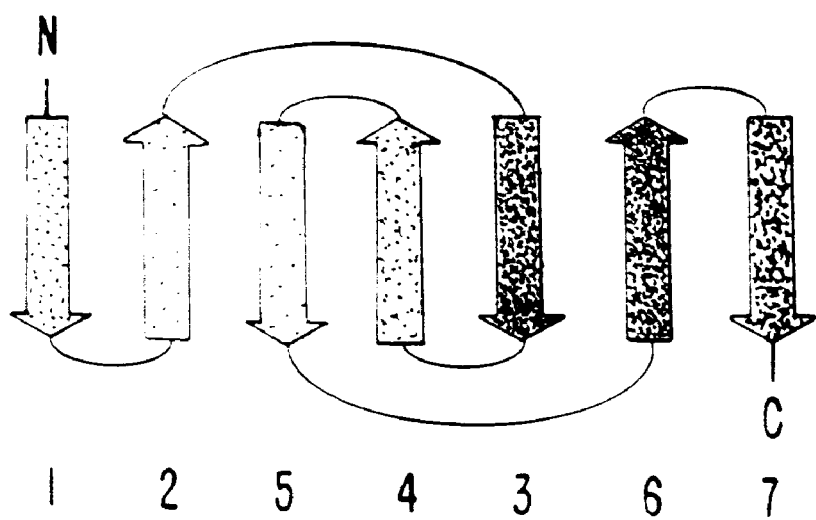
Figures 4A, 4B:
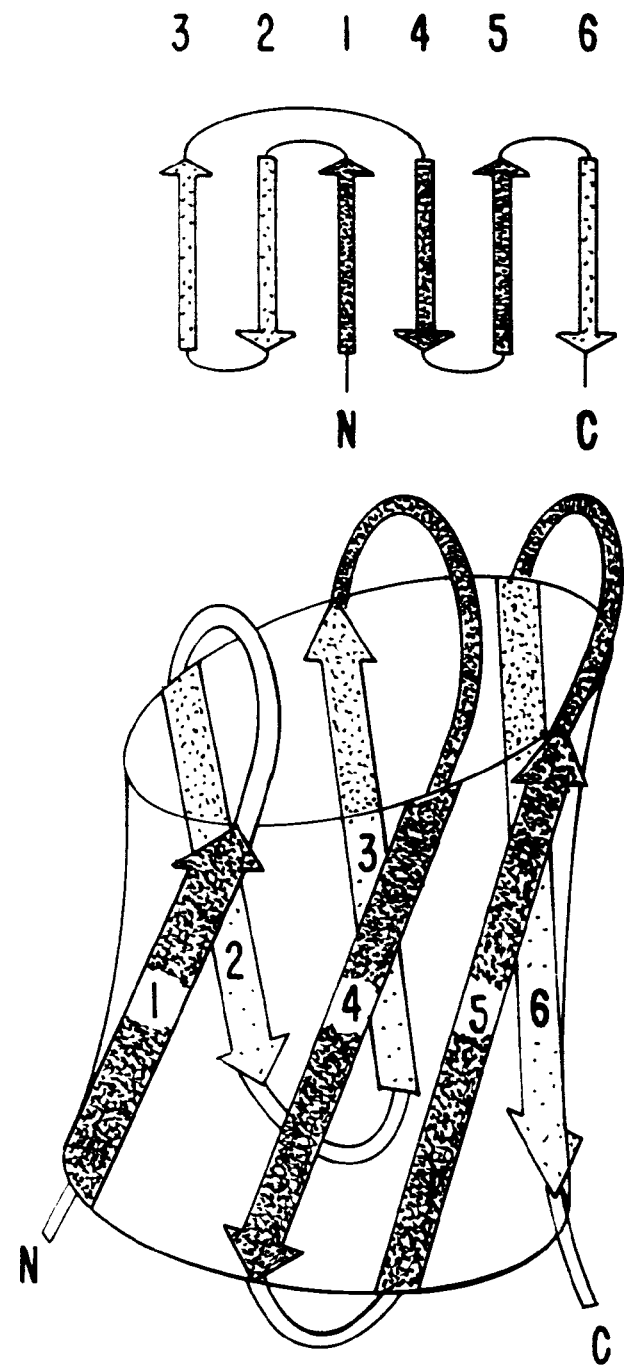
FIG. 4 is a topology diagram of the domain structure of chymotrypsin. The chain is folded into a Greek key motif followed by a hairpin motif that are arranged as a six stranded antiparallel β barrel.

The invention is also in the placement and segmentation of the enzymatic sequence. For example, those domains of the inserted enzyme sequence which are spatially located in or around the active site and or those residues which may play a role in extensive specific substrate binding are placed in those regions which are capable of the highest diversification (e.g., the CDR regions). For example, chymotrypsin also folds in an antiparallel beta barrel like an immunoglobulin domain (see FIG. 2 and 3). The active site and substrate specificity regions are located in the protein sequence bridging beta strands of the beta barrel as are the CDR regions in an immunoglobulin variable region.

The invention is also in a varying array of chimeric antibody/enzyme structures. In one embodiment the enzymatic sequences replaces one or multiple variable domains. Further multiple different enzymatic sequences may be integrated into the germline in an analogous fashion to the multiple V, D and J variable regions to create an extensively altered germline and to further increase diversification. In another embodiment the enzymatic sequence with inserted variable region intronic spacing and signal sequences may be inserted into the germline so as to incorporate the enzymatic domain as an amino terminal fusion. In another embodiment such amino terminal enzymatic fusions may have antibody variable regions replaced with constant immunoglobulin regions thereby limiting diversification to only the enzymatic region. In another embodiment of the invention sequences encoding enzymatic functionality are inserted into the germline antibody locus such that the enzyme sequence is subject to immunoglobulin variable region diversification, but is not covalently linked to an immunoglobulin domain. A wide variety of such different structures may be utilized and employed in the invention by one skilled in the art.

The invention is also in the method and sequence of production of catalytic antibodies using the altered germline animals of the invention. For example, immunization with a variety of different TSA types, inhibitors, and/or suicide substrates (see Suzuki; Thorn; U.S. Pat. Nos. 4,792,446;4, 963,355; 5,156,965; 5,401,641, which are incorporated herein by reference) may be carried out in a sequential fashion to elicit antibodies with increasing affinity. In another embodiment after immunization of the animals of the invention a resulting enzymatic antibody sequence is then transgenically integrated into the germline sequence of another animal. For example, this technique can be useful in the stepwise iterative evolution of a catalytic antibody. In this way evolutionary progress may be continued at a germline level.

The immune system selects antibodies based on binding affinity and/or binding kinetics. An enzyme with high turnover rates is required to bind the reactant, catalyzed the formation of the product and release the product to allow access of another reactant to the functional active site of the enzyme. Whereas a high turnover rate enzyme requires the release of the product an antibody is selected for high binding affinity. In another embodiment of the invention the transgenically inserted enzymatic or catalytic functional unit is selectively altered with the relatively small set of mutations so as to substantially lower the catalytic activity (e.g., mutation of the catalytic triad residues of a serine protease). In this way the substrate of interest may be used as an antigen and selectivity for the desired substrate may be achieved. After selection for binding/selectivity the small set of mutations are reverted (e.g., through specific mutation, in vitro screening, selection, etc.) in order to increase the catalytic turnover. The resulting catalytic antibody may be further selected using enzymatic inhibitor, suicide substrates and/or TSA's.

The invention is in the iterative immunization of the altered germline animals of the invention and also in the simultaneous immunization with multiple antigens. Iterative immunization may use the same antigen or different antigens to tailor the progression of the immune response. Multiple antigens may be delivered simultaneously to bias the immune response as desired. Many techniques are available to one skilled in the art to optimize antibody production. For example, adjuvants may be employed to heightened an immune response.

The antibodies with enzymatic activity of the current invention may be modified through techniques known in the art. For example, three dimensional structural information may be used for rational design modifications of the catalytic antibodies. In a further example, in vitro mutagenesis and screening and or selection may be employed to further develop the enzymatic antibodies of the current invention.

The pre-generation of a certain level of diversity can be advantageous for the selection of the desired enzyme activity using the methods of the invention. Examples of mutagenesis methods to generate enzyme gene fragments with increased diversity, by generating a number of differing and mutated gene fragments for incorporation in place of multiple immunoglobulin gene elements i.e., V, D and or J regions, follows below. In the immunoglobulin gene loci existing diversity is used and matched with methods for generation of diversity. Thus, it would be advantageous to introduce multiple copies of the enzyme fragments of interest to enhance the mechanism of diversity selection in a similar fashion to that used in the generation of antibody diversity.

Various mutagenesis methods are known to the art for the generation of diversity. In one method a synthetic gene construction is made using 'doped' sequences which contain the catalytic engine's sequence of interest, but with the bases used in the synthesis of the oligonucleotides 'doped' with the other 3 bases at a low level, typically from 0.1–10%. In this synthesis the catalytic site is not subject to mutation or is subject to mutation only at a lower level relative to the other sequences. This method generates a family of sequences which are mutated at every base only 0.1–10% of the time based on the original sequence. These synthetic oligonucleotides are then assembled into the final gene using various standard methods.

In an alternative method, the gene of interest would also be constructed as outlined above using synthetic oligonucleotides, but now with very defined portions of the sequence incorporating specific sites which are totally randomized with respect to the potential codons. This can be achieved by the use of mixed bases used in the synthesis of the oligonucleotide or by the use of pre-made codons used during the synthesis of the oligonucleotides for the gene synthesis. These mutated gene fragments would then be subjected to assembly as outlined above.

In another alternative method, the gene of interest would also be constructed based on the use of PCR with limiting or unnatural bases to generate a gene fragment with mutated bases. These mutated gene fragments would then be subjected to assembly as outlined above.

In still another alternative method, the gene of interest would also be constructed based on the use of chemical methods to modify the bases, i.e., dimethyl sulphate, bisulphite, formic acid, hydrazine etc. These mutated gene fragments would then be subjected to assembly as outlined above.

The result of these types of gene construction is a pool of mixed genes which can then be cloned into the immunoglobulin loci using various methods known to the art (see examples). For example, the genes might be co-ligated with a pool of clone non coding sequences isolated from the immunoglobulin V region loci. Alternatively, other 'stuffer' sequences could be used based on the desire to generate a series of interspersed enzyme gene sequence portions analogous to the V region gene families. In addition, the gene fragments could be specifically inserted in place of the V, D or J region gene sequences. These modified and or reconstructed psudeo loci would then be cloned into a cosmid vector and clones screened for the size and number of the enzyme gene sequence portions. The clone with the best number and size fragment would then be subjected to recombination into the immunoglobulin loci mini gene loci in the YAC vector (see examples). This recombination would be achieved via the 5' and 3' fragments (of the selected insertion site) of the immunoglobulin gene loci of choice.

Dimeric enzyme active sites are discussed below. As the immunoglobulin and T cell receptors diversity is also due in part to the combinatorial diversity generated from two separate variable region genes i.e., light and heavy chain variable regions of the immunoglobulin loci. The use of the immunoglobulin and T cell receptors mechanisms for generation of diversity are uniquely suited to enzymes composed of two sequences (or subunits) which together make the active enzyme. The two subunits could be from the same gene as a dimer, the same gene as a fragmented protein, or from two differing genes. Examples of enzymes forming an active site at the interface of a homodimer are Ornithine decarboxylase, aspartate transcarbamylase, 3-hydroxy-3-methylglutaryl CoA reductase, Pyruvate decarboxylase, dethiobiotin synthetase and glucose oxidase (Alexeev D et al Structure 1994, 2; 1061. Osterman A et al Biochemistry 1994, 33; 13662. Frimpong K et al 1994, 269; 1217. Dyda F et al 1993 32; 6165. Hecht HJ et al 1993, 229; 153). These enzymes forming the active site from two subunits also generate two active sites in the homodimer or a single active site when one of the proteins in the dimer has a single mutation in the active site.

In the present invention the enzyme gene fragments would be incorporated into both the heavy and light chain loci and mice generated from the ES cell lines containing these modified gene loci. The light and heavy chain modified loci would then be combined by crosses between the transgenic mice. The mice with both of the loci modified would thus be able to expand the level of diversity possible through the combinatorial diversity possible.

One skilled in the art would realize that a wide variety of species may be utilized to generate catalytic antibodies. For example, mice, rats, rabbits, goats, sheep, cows, etc. as well as non-mammalian species may be used. Further one skilled in the art would realize that a wide variety of enzymatic functionalities and enzyme families as well as specific enzymes may be utilized in the invention (U.S. Pat. Nos. 4,792,446; 4,963,355; 5,156,965; 5,401,641; 5,229,272; 5,194,585; 5,236,836, which are incorporated herein by reference).

The following examples, which illustrate the methods of the present invention, utilize the following methods and materials The transgenic mice are derived according to Hogan, et al., "Manipulating the Mouse Embryo: A Laboratory Manual", Cold Spring Harbor Laboratory, which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., Nature 342:435–438 (1989); and Schwartzberg et al., Science 246:799–803 (1989), each of which is incorporated herein by reference).

DNA cloning procedures are carried out according to J. Sambrook, et al. in Molecular Cloning: A Laboratory Manual., 2d ed., 1989, Cold Spring Harbor Laboratory Press, Cold Spring Harbor, N.Y., which is incorporated herein by reference.

Hybridoma cells and antibodies are manipulated according to "Antibodies: A Laboratory Manual", Ed Harlow and David Lane, Cold Spring Harbor Laboratory (1988), which is incorporated herein by reference.

EXAMPLE I

Incorporation of the 5' or amino terminal portion of the enzyme lysozyme into the heavy chain region of the mouse germline by recombination to allow the reconstruction and selection of active enzymes using the immunoglobulin recombination and somatic mutation mechanisms.

Initially the VH81X (mouse equivalent VH most proximal to the D region, Nature 311,727–753 ,1984) heavy chain variable region is isolated from a phage library using a synthetically made oligonucleotide probe to screen a genomic lambda library phage derived from mouse fetal liver DNA (Stratagene). This V region gene fragment is then subcloned into a plasmid vector containing the herpes simplex thymidine kinase (tk) gene driven by the mouse phosphoglycerate kinase gene (PGK) promoter (WO 94/02602) to give vector pVH81X. Plasmid pVH81X is used to allow the subcloning of the 5' portion of the lysozyme gene in place of the VH81X coding sequence, but with the prepeptide and recombination signals intact. In this example the 5' portion of lysozyme spans from amino acid Lys 1 to Gly 71 ( Lysozyme EC3.2.1.17, Jung et al, "Encode functional and structural units of chicken lysozyme", National Academy of Science U.S.S. 77 (10), 5759–5763, 1980 which is incorporated herein by reference). It will be understood that various portions of the enzyme could be placed into this construct based on the desired recombination pathway.

The construct is made by using PCR to generate three fragments with identical sequence overlaps to allow the sequential construction of the chimeric genomic gene.

These three fragments are 1) the 5' portion of the VH81X gene including the non coding region; 2) the 5' portion of the lysozyme gene with VH region sequences at the 5' and 3' ends of the fragments after the PCR and; 3) the 3' end of the VH gene. The construction would consist of combining 1) and 2) in to PCR with the 5' primer from the PCR 1) and the 3' primer from PCR 2) to generate a fragment to contain the sequences of 1) and 2). The product of the PCR reaction combining fragments 1) and 2) are added to the products of PCR 3) and the 5' primer from the PCR 1) is combined with the 3' primer from PCR3) and again subjected to PCR, this would result in the final PCR fragment which would have incorporated fragments 1) 2) and 3) into a single fragment. This final fragment combining 1) 2) and 3) and containing the 5' portion of lysozyme within the genomic sequences of the VH81X V region gene is then cloned in to pVH81X replacing the natural sequence and generating the vector pVHLYS5 for recombination into the germline of the mouse. The plasmid pVHLYS5 is made ready for recombination after the insertion of the neo gene within this new genomic sequence 3' to fragment 3) generating pVHLYS5 neo (see FIG. 5a).

This recombination vector is constructed such that at least 1 kb of native genomic sequence is flanking the modified VH81X gene element with the 5' portion of the lysozyme sequence.

The vector pVHLYS5 neo is linearized and used for electroporation of the embryonic stem cell line using standard methods. The cells from the transfection are then selected on media containing G418 to select for the neo gene and gancylovir (Syntex) to select the loss of the thymidine kinase gene. This double selection protocol improves the recovery of the homologous recombination events resulting in the replacement of the VH81X gene. The resulting colonies are then expanded in the absence of the gancyclovir and tested for the specific insertion by southern blot analysis which generates a new sized gene fragment which hybridizes to the 5' gene fragment of lysozyme used in the construction of the recombination vector.

From a screen of 300 cell lines those with the desired fragments are expanded and subject to further analysis.

The cell line with its inserted 5' portion of the lysozyme gene, LYS5 is expanded ready for a second round of electroporation to generate the final cell line containing both portions of the lysozyme gene within the heavy chain recombination units.

EXAMPLE II

Incorporation of the 3' or carboxy terminal portion of the enzyme lysozyme into the heavy chain region of the mouse germline by recombination to allow the reconstruction and selection of active enzymes using the immunoglobulin recombination and somatic mutation mechanisms.

Initially the JH heavy chain J regions is isolated from a phage library using a synthetically made oligonucleotide probe to screen a genomic lambda library phage derived from mouse fetal liver DNA (Stratagene). This JH region gene fragment is then subcloned into a plasmid vector containing the herpes simplex thymidine kinase (tk) gene driven by the mouse phosphoglycerate kinase gene (PGK) promoter (WO 94/02602) to give vector pJH. Plasmid pJH is used to allow the subcloning of the 3' portion of the lysozyme gene in place of the four JH coding sequences, but with both recombination signals intact. In this example the 3' portion of lysozyme spans from amino acid Leu 75 to Leu 129. It will be understood that various portions of the enzyme could be placed into this construct based on the desired recombination pathway.

The construct is made by using PCR to generate three fragments with identical sequence overlaps to allow the sequential construction of the chimeric genomic gene.

These three fragments are 1) the 5' portion of the JH gene cluster (the non coding region including the most 5' recombination signals); 2) the 3' portion of the lysozyme gene now with JH region sequences at the 5' and 3' ends of the fragments and; 3) the 3' end of the JH gene cluster containing the most 3' recombination signal. The construction would consist of combining 1) and 2) in to PCR with the 5' primer from the PCR 1) and the 3' primer from PCR 2) to generate a fragment to contain the sequences of 1) and 2). The product of the PCR reaction combining fragments 1) and 2) are added to the products of PCR 3) and the 5' primer from the PCR 1) is combined with the 3' primer from PCR3)

and again subjected to PCR, this would result in the final PCR fragment which would have incorporated fragments 1) 2) and 3) into a single fragment. This final fragment combining 1) 2) and 3) and containing the 3' portion of lysozyme within the genomic sequences of the JH region gene is then cloned in to pJH replacing the natural sequence and generating the vector pJHLYS3 for recombination into the germline of the mouse. The plasmid pJHLYS3 is made ready for recombination after the insertion of the hygromycin gene within this new genomic sequence 3' to fragment 3) generating pJHLYS3hyg (see FIG. 5b).

This recombination vector is constructed such that at least 1 kb of native genomic sequence is flanking the modified JH gene element with the 3' portion of the lysozyme sequence.

The vector pJHLYS3hyg is linearized and used for electroporation of the cell line with its inserted 5' portion of the lysozyme gene, LYS5, using standard methods. The cells from the transfection are then selected on media containing hygromycin to select for the hyg gene and gancylovir (Syntex) to select the loss of the thymidine kinase gene. This double selection protocol improves the recovery of the homologous recombination events resulting in the replacement of the JH gene cluster. The resulting colonies are then expanded in the absence of the gancyclovir and tested for the specific insertion by southern blot analysis which generates a new sized gene fragment which hybridizes to the 3' gene fragment of lysozyme used in the construction of the recombination vector.

From a screen of 300 cell lines those with the desired fragments are expanded and subject to further analysis.

The cell line LYS53 is constructed with three amino acids missing from the combination of 5' and 3' gene fragments (Ser 72, Lys 73 and Asn 74) this is to allow the incorporation of the D regions in the recombination pathway. This creates a hot spot for mutagenesis in the lysozyme structure for this 5' and 3' gene fragment combination.

The cell line with its inserted 5' and 3' portions of the lysozyme gene, LYS53 is expanded ready for use. This cell could form the basis of a new mouse via generation of chimeric mice and breeding. Alternatively this cell line could be used for the isolation of a gene fragment containing the 5' and 3' lysozyme genes flanked by the native mouse sequences. These gene fragments when put directly into the nucleus of single cell mouse embryos would give rise to mice containing the mutated immunoglobulin genes.

EXAMPLE III

Incorporation of the 5' or amino terminal portion of the enzyme lysozyme into the kappa light chain region of the mouse germline by recombination to allow the reconstruction and selection of active enzymes using the immunoglobulin recombination and somatic mutation mechanisms.

Initially the VK light chain variable region is isolated from a phage library using a synthetically made oligonucleotide probe to screen a genomic lambda library phage derived from mouse fetal liver DNA (Stratagene). This V region gene fragment is then subcloned into a plasmid vector containing the herpes simplex thymidine kinase (tk) gene driven by the mouse phosphoglycerate kinase gene (PGK) promoter (WO 94/02602) to give vector pVK. Plasmid pVK is used to allow the subcloning of the 5' portion of the lysozyme gene in place of the VK coding sequence, but with the prepeptide and recombination signals intact. In this example the 5' portion of lysozyme spans from amino acid Lys 1 to Asn 74. It will be understood that various portions of the enzyme could be placed into this construct based on the desired recombination pathway.

The construct is made by using PCR to generate three fragments with identical sequence overlaps to allow the sequential construction of the chimeric genomic gene.

These three fragments are 1) the 5' portion of the VL gene including the non coding region; 2) the 5' portion of the lysozyme gene now with VL region sequences at the 5' and 3' ends of the fragments and; 3) the 3' end of the VL gene. The construction would consist of combining 1) and 2) in to PCR with the 5' primer from the PCR 1) and the 3' primer from PCR 2) to generate a fragment to contain the sequences of 1) and 2). The product of the PCR reaction combining fragments 1) and 2) are added to the products of PCR 3) and the 5' primer from the PCR 1) is combined with the 3' primer from PCR3) and again subjected to PCR, this would result in the final PCR fragment which would have incorporated fragments 1) 2) and 3) into a single fragment. This final fragment combining 1) 2) and 3) and containing the 5' portion of lysozyme within the genomic sequences of the VL V region gene is then cloned in to pVL replacing the natural sequence and generating the vector pVKLYS5 for recombination into the germline of the mouse. The plasmid pVKLYS5 is made ready for recombination after the insertion of the neo gene within this new genomic sequence 3' to fragment 3) generating pVKLYS5neo (see FIG. 6a).

This recombination vector is constructed such that at least 1 kb of native genomic sequence is flanking the modified VL gene element with the 5' portion of the lysozyme sequence.

The vector pVKLYS5 neo is linearized and used for electroporation of the embryonic stem cell line using standard methods. The cells from the transfection are then selected on media containing G418 to select for the neo gene and gancylovir (Syntex) to select the loss of the thymidine kinase gene. This double selection protocol improves the recovery of the homologous recombination events resulting in the replacement of the VL gene. The resulting colonies are then expanded in the absence of the gancyclovir and tested for the specific insertion by southern blot analysis which generates a new sized gene fragment which hybridizes to the 5' gene fragment of lysozyme used in the construction of the recombination vector.

From a screen of 300 cell lines those with the desired fragments are expanded and subject to further analysis.

The cell line with its inserted 5' portion of the lysozyme gene, LYS5K is expanded ready for a second round of electroporation to generate the final cell line containing both portions of the lysozyme gene within the heavy chain recombination units.

EXAMPLE IV

Incorporation of the 3' or carboxy terminal portion of the enzyme lysozyme into the light chain region of the mouse germline by recombination to allow the reconstruction and selection of active enzymes using the immunoglobulin recombination and somatic mutation mechanisms.

Initially the JK heavy chain J region is isolated from a phage library using a synthetically made oligonucleotide probe to screen a genomic lambda library phage derived from mouse fetal liver DNA (Stratagene). This JK region gene fragment is then subcloned into a plasmid vector containing the herpes simplex thyridine kinase (tk) gene driven by the mouse phosphoglycerate kinase gene (PGK) promoter (WO 94/02602) to give vector pJK. Plasmid pJK is used to allow the subcloning of the 3' portion of the lysozyme gene in place of the four JK coding sequences, but with both recombination signals intact. In this example the 3' portion of lysozyme spans from amino acid Leu 75 to Leu 129. It will be understood that various portions of the enzyme could be placed into this construct based on the desired recombination pathway.

The construct is made by using PCR to generate three fragments with identical sequence overlaps to allow the sequential construction of the chimeric genomic gene.

These three fragments are 1) the 5' portion of the JK gene cluster (the non coding region including the most 5' recombination signals); 2) the 3' portion of the lysozyme gene now with JK region sequences at the 5' and 3' ends of the fragments and; 3) the 3' end of the JK gene cluster containing the most 3' recombination signal. The construction would consist of combining 1) and 2) in to PCR with the 5' primer from the PCR 1) and the 3' primer from PCR 2) to generate a fragment to contain the sequences of 1) and 2). The product of the PCR reaction combining fragments 1) and 2) are added to the products of PCR 3) and the 5' primer from the PCR 1) is combined with the 3' primer from PCR3) and again subjected to PCR, this would result in the final PCR fragment which would have incorporated fragments 1) 2) and 3) into a single fragment. This final fragment combining 1) 2) and 3) and containing the 3' portion of lysozyme within the genomic sequences of the JH region gene is then cloned in to pJK replacing the natural sequence and generating the vector pJKLYS3 for recombination into the germline of the mouse. The plasmid pJKLYS3 is made ready for recombination after the insertion of the hygromycin gene within this new genomic sequence 3' to fragment 3) generating pJKLYS3hyg (see FIG. 6b).

This recombination vector is constructed such that at least 1 kb of native genomic sequence is flanking the modified JK gene element with the 3' portion of the lysozyme sequence.

The vector pJKLYS3hyg is linearized and used for electroporation of the cell line with its inserted 5' portion of the lysozyme gene, LYS5, using standard methods. The cells from the transfection are then selected on media containing hygromycin to select for the hyg gene and gancylovir (Syntex) to select the loss of the thymidine kinase gene. This double selection protocol improves the recovery of the homologous recombination events resulting in the replacement of the JH gene cluster. The resulting colonies are then expanded in the absence of the gancyclovir and tested for the specific insertion by southern blot analysis which generates a new sized gene fragment which hybridizes to the 3' gene fragment of lysozyme used in the construction of the recombination vector.

From a screen of 300 cell lines those with the desired fragments are expanded and subject to further analysis.

The cell line with its inserted 5' and 3' portions of the lysozyme gene, LYS53K is expanded ready for use. This cell could form the basis of a new mouse via generation of chimeric mice and breeding. Alternatively this cell line could be used for the isolation of a gene fragment containing the 5' and 3' lysozyme genes flanked by the native mouse sequences. These gene fragments when put directly into the nucleus of single cell mouse embryos would give rise to mice containing the mutated immunoglobulin genes.

EXAMPLE V

Generation of the germline chimeras.

The transfected ES cell lines LYS53 and LYS53K are cultured following standard methods, trypsinized and resuspended in injection medium (DMEM 15% fetal calf serum, 20 mM HEPES, pH 7.3, antibiotics and 2-mercaptoethanol). Three and half day old C57BL/6L (Jackson Labs Bar Harbor, Me.) blastocysts are obtained from 4–5 week old superovulated females following standard methods.

About 10 to 15 cells are injected into the blastocoel of each blastocyst. These ES-cells containing blastocysts are then surgically transferred to one uterine horn of C57BL/6L X DBA/2 or CS7BL/6J X CAB F1 pseudopregnant females.

The contribution of the ES cells to the offspring is determined by examination of the coat color. The chimeric offspring in which the ES cells participate in the formation of the animals have coats containing agouti and cream hairs.

The germline contribution of the selected chimeric mice is determined by mating with C57BL/6J mice and counting the expected F1 offspring for the agouti color. About 50% of the agouti mice would be expected to inherit the mutated heavy chain or kappa chain gene loci. The germline transmission is further characterized by the southern blot analysis of the DNA isolated from the tails of the F1 progeny.

These F1 mice are then subjected to an intercross to isolate the homozygote mice with respect to the mutated heavy chain or kappa chain gene loci. These mice would now form the basis of a mouse colony to isolate recombined lysozyme activity for altered substrate specificity but still retaining the active catalytic site residues Glu 35 and Asp 52.

EXAMPLE VI

An alternative method to generate the transgenic mice containing the enzyme recombination system.

The generation of transgenic mice containing the enzyme modified heavy chain gene loci isolated from the ES cell line LYS53. The LYS53 cell line is culture up and the modified heavy chain minilocus isolated as a fragment containing the modified VH291 gene now with lysozyme 5', the D region genomic sequences, the JH region now containing the lysozyme 3' portion in place of the six JH genes, the mu heavy chain sequence. This gene fragment is isolated by cloning into a YAC library and screening using a probe of the lysozyme gene. The YAC clone with the fewest extra VH genes 5' to the modified VH291 (most 5' proximal VH gene to the JH region) is grown up and the DNA used to transfect an ES cell line. The transfectants are selected using G418 for the neo gene present in the modified gene. The resulting resistant ES cell lines are then characterized with respect to the desired gene insertion. The clone with the intact modified heavy chain loci are then cultured and used for the generation of chimeric mice as described in example V. The resulting mice would contain the full native antibody system in combination with the modified heavy chain miniloci.

Figure 7:
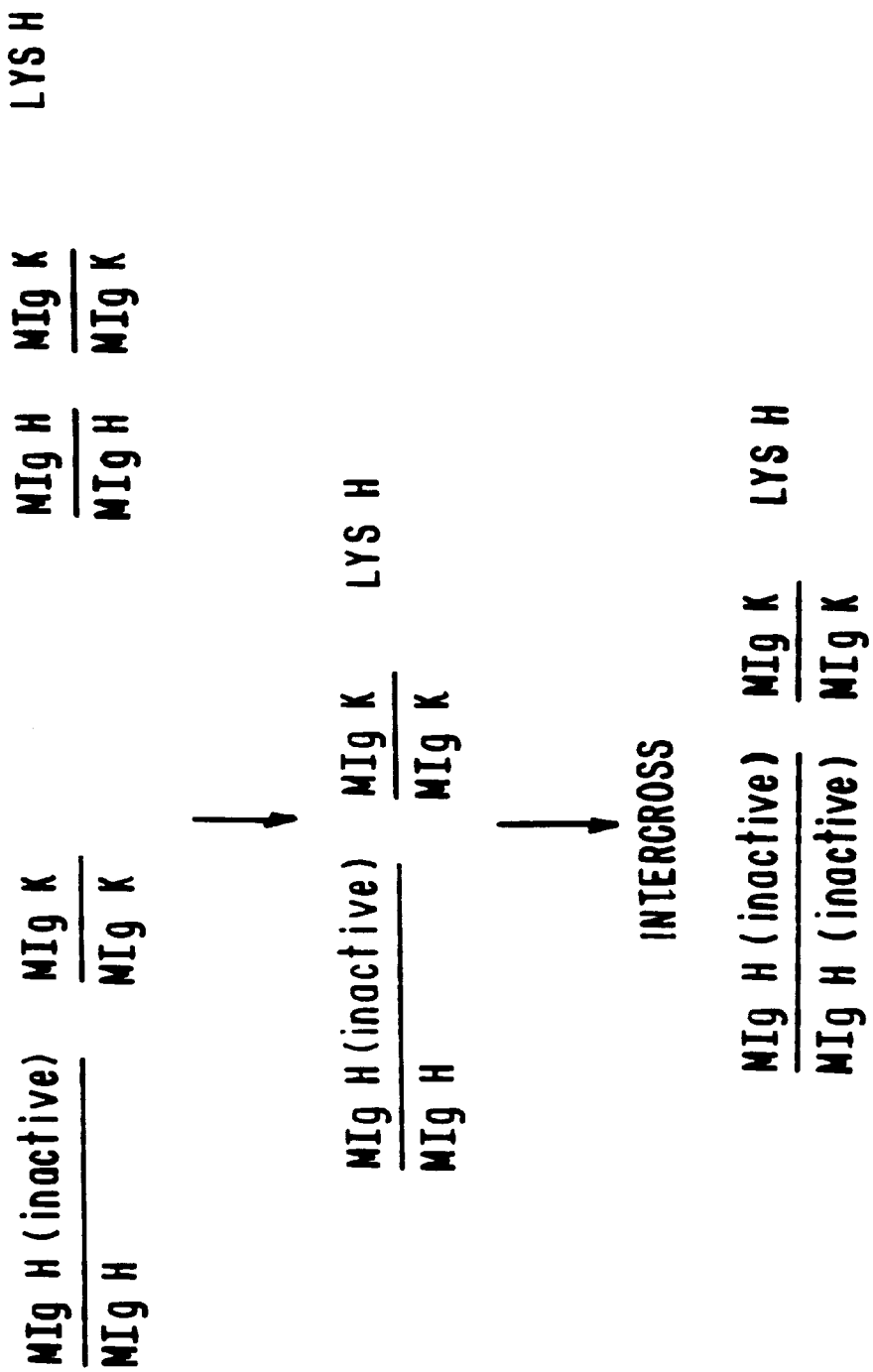
FIG. 7 is a flow diagram showing crossing of mice which produces progeny which are homozygote with respect to the inactive heavy chain loci but containing the lysozyme modified heavy chain miniloci.

These first generation mice are the crossed with mice which are heterozyogotes with respect to a defective immunoglobulin heavy chain loci (produced according to standard methods WO 94/02602). This results in progeny which contain the combination of i) heterozyogotes with respect to a defective immunoglobulin heavy chain and ii) the modified heavy chain miniloci. These progeny with the double modifications are then subject to an intercross which results in the production of a homozygote with respect to the inactive heavy chain loci but containing the lysozyme modified heavy chain miniloci. (see FIG. 7).

Figure 8:
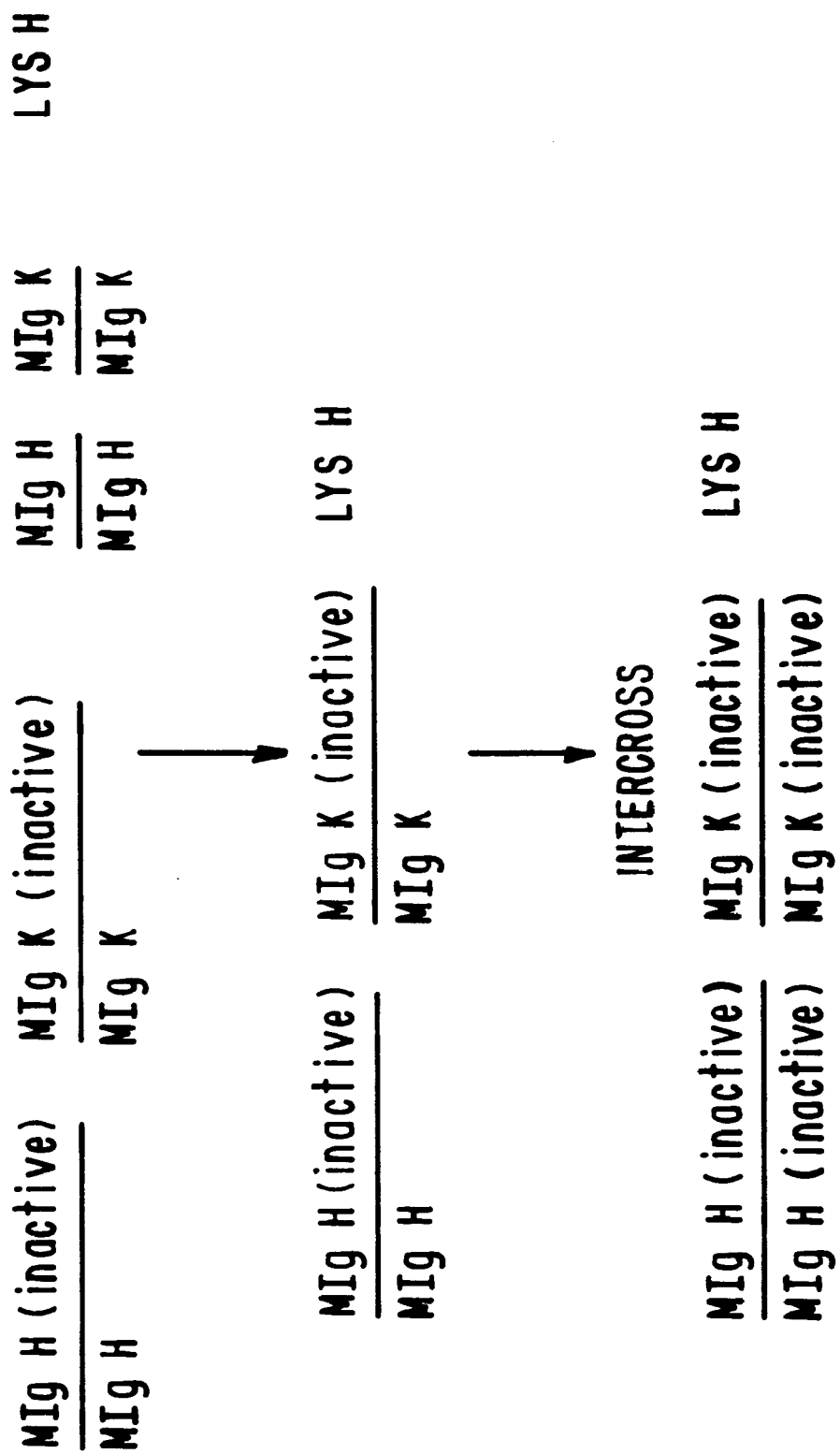
FIG. 8 is a flow diagram showing crossing of mice which produces progeny which are homozygote with respect to the inactive heavy chain and light chain loci but containing the lysozyme modified heavy chain miniloci.

In an alternative to the above breeding route these first generation mice are then crossed with mice which are heterozyogotes with respect to a defective immunoglobulin heavy chain loci and immunoglobulin kappa light chain loci (produced according to standard methods WO 94/02602). This results in progeny which contain the combination of i) heterozyogotes with respect to a defective immunoglobulin heavy chain and kappa light chain and ii) the modified heavy chain miniloci. These progeny with the double modifications are then subject to an intercross which result in the production of a homozygote with respect to the inactive heavy chain and light chain loci but containing the lysozyme modified heavy chain miniloci. (see FIG. 8).

These mice with the double and triple modified antibody genes are now ready for the selection of new catalytic activities for lysozyme based on immunization to drive the recombination and somatic mutation of the new heavy chain mini loci containing the lysozyme gene fragments.

EXAMPLE VII

An alternative method to generate the transgenic mice containing the enzyme recombination system.

The generation of transgenic mice containing the enzyme modified heavy chain gene loci isolated from the ES cell line LYS53K. The LYS53K cell line is culture up and the modified light chain minilocus isolated as a fragment containing the modified VK gene now with lysozyme 5', the JK region now containing the lysozyme 3' portion in place of the JK genes, the kappa light chain sequence. This gene fragment is isolated by cloning into a YAC library and screening using a probe of the lysozyme gene. The YAC clone with the fewest extra VK genes 5' to the modified VK (most 5' proximal VK gene to the JK region) is grown up and the DNA used to transfect an ES cell line. The transfectants are selected using G418 for the neo gene present in the modified gene. The resulting resistant ES cell lines are then characterized with respect to the desired gene insertion. The clone with the intact modified heavy chain loci are then cultured and used for a the generation of chimeric mice as described in example V. The resulting mice would contain the full native antibody system in combination with the modified kappa chain miniloci.

Figure 9:
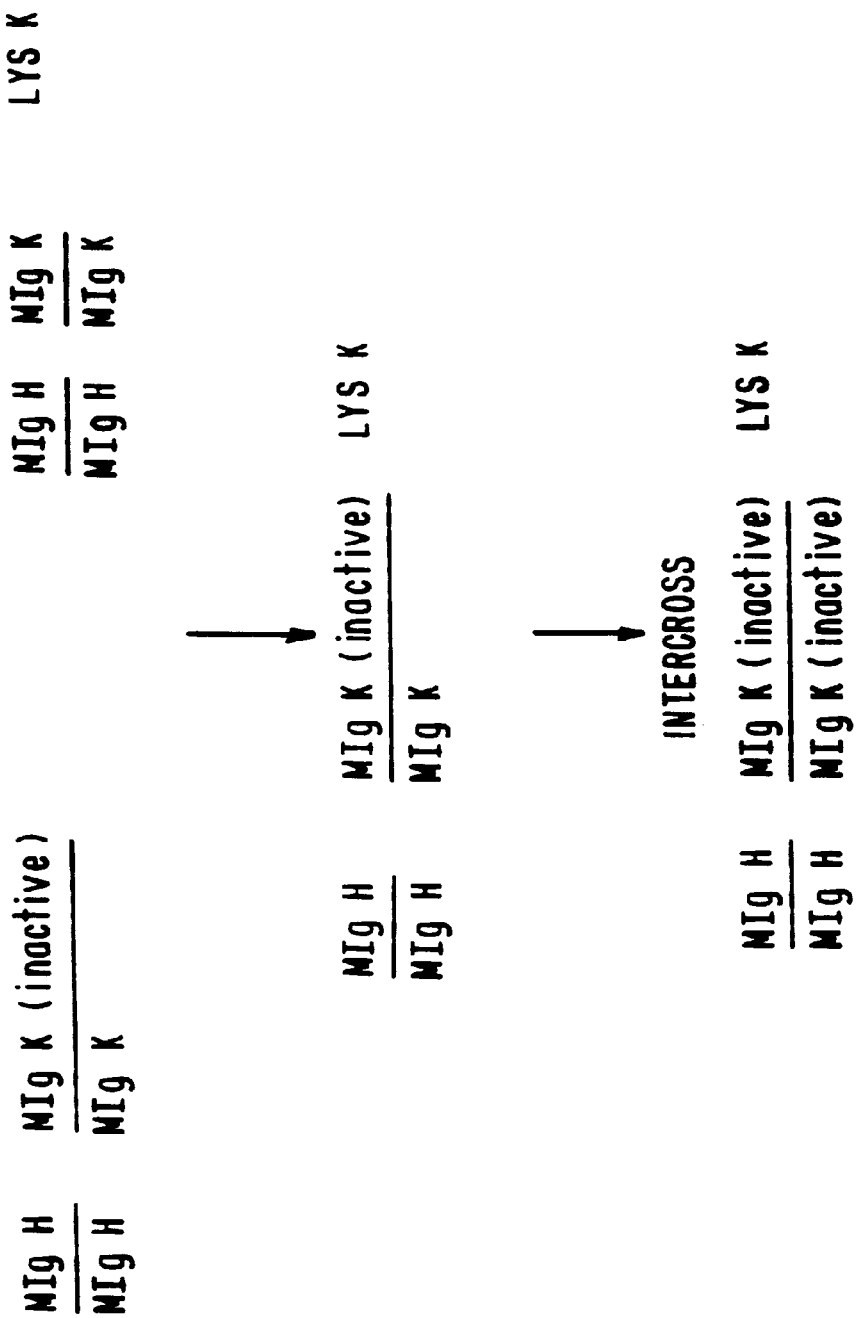
FIG. 9 is a flow diagram showing crossing of mice which produces progeny which are homozygote with respect to the inactive heavy chain and light chain loci but containing the lysozyme modified light chain kappa miniloci.

These first generation mice are then crossed with mice which are heterozyogotes with respect to a defective immunoglobulin light chain loci (produced according to standard methods WO 94/02602). This results in progeny which contain the combination of i) heterozyogotes with respect to a defective immunoglobulin light chain and ii) the modified light chain kappa miniloci. These progeny with the double modifications are then subject to an intercross which result in the production of a homozygote with respect to the inactive light chain loci but containing the lysozyme modified light chain kappa miniloci. (see FIG. 9)

These mice with the double modification are now ready for the selection of new catalytic activities for lysozyme based on immunization to drive the recombination and somatic mutation of the new heavy chain mini loci containing the lysozyme gene fragments.

EXAMPLE VIII

Incorporation of the enzyme ribonuclease A into the heavy chain region of the mouse immunoglobulin gene loci by recombination in yeast to generate a miniloci for generation of chimeric mice producing new ribonuclease activities.

Ribonuclease A 5' fragment from amino acid 1 to 68 (Ribonucleaese A EC 3.1.27.5, see Borkakoti et al "The Refined Structure Of Ribonuclease-A at 1.45 Angstroms Resolution", J. Crystallographic Spectroscopy Res. 14, 467 1984, which is incorporated herein by reference).

The ribonuclease A gene is constructed from synthetic oligonucleotides between 50 and 70 bases long. The whole gene including selected restriction sites is encoded in 8 oligonucleotides. The gene is assembled and ligated followed by PCR with the 5' and 3' oligonucleotides to amplify the ligated gene fragment. The gene is then cloned in to a plasmid vector p5R. PCR is used to generate two fragments which correspond to i) the 5' portion of the most proximal heavy chain variable region, containing the prepeptide and 800 bases 5', and ii) the 3' portion of the most proximal heavy chain variable region, containing the recombination signals and 800 bases 3' using the YAC clone described in Example 9 containing the VH, D, JH and Mu heavy chain gene fragment. The 5' PCR fragment is cloned into the selected restriction site on the 5' end of the 5' portion of the Rnase gene 10 fragment. The 3' PCR fragment is cloned into the selected restriction site on the 3' end of the 5' portion of the Rnase gene fragment. This vector p5RREC is used as the source of the gene fragment containing the 5' portion of the mase gene flanked by the immunoglobulin gene. This gene fragment is then cloned into half a YAC vector which includes a yeast selectable marker HIS3 not present in the original YAC vector, a centromere (CEN) and a single telomere (TEL) to generate p5RRECY.

Ribonuclease A 3' fragment from amino acid 72 to 124 (see Borkakoti reference incorporated above).

The ribonuclease A gene is constructed from synthetic oligonucleotides between 50 and 70 bases long. The whole gene including selected restriction sites is encoded in 8 oligonucleotides. The gene is assembled and ligated followed by PCR with the 5' and 3' oligonucleotides to amplify the ligated gene fragment. The gene is then cloned in to a plasmid vector p3R. PCR is then used to generate two fragments which correspond to i) the 5' portion of the most 5' JH region, containing the recombination signals and 800 bases 5', and ii) the 3' portion of the most 3' JH region, containing the recombination signals and 800 bases 3' using the YAC clone described in Example 9 containing the VH, D, JH and Mu heavy chain gene fragment. The 5' PCR fragment is cloned into the selected restriction site on the 5' end of the 5' portion of the Rnase gene fragment. The 3' PCR fragment is cloned into the selected restriction site on the 3' end of the 5' portion of the Rnase gene fragment. This vector p3RREC is used as the source of the gene fragment containing the 3' portion of the mase gene flanked by the immunoglobulin genomic sequences.

The modified JH region subclone containing the 3' portion of the enzyme of interest from p3RREC is also subcloned into half a YAC vector which includes a yeast selectable marker LEU2 not present in the original YAC vector, and a single TEL giving rise to p3RRECY.

Following the construction of these vectors the half YAC vector with the modified VH gene (p5RRECY) is linearized and used to transform a yeast strain which carries the desired mouse heavy chain sequences of the VH, D JH and Mu heavy chain. Selection for the histidine prototrophy gives rise to yeast colonies that have undergone homologous recombination. The half YAC vector containing the enzyme modified JH region containing the 3' portion of the enzyme of interest (p3RRECY) is then linearized and used to transform the yeast strain generated in the previous step. Selection for leucine-prototropy results in a yeast strain containing the whole enzyme/immunoglobulin loci. Preferably, both selection steps can be carried out together. This YAC is isolated and microinjected into ES cell and the cell subjected to neo selection using G418. The resulting cell line RNA35YAC is then used to generate a chimeric mouse as described above in example V. The resulting chimeric mouse is then subjected to breeding in order to generate mice producing the enzyme antibody chimeric molecule with out the production of native antibodies. Examples 6 and 7 describe breeding protocols to remove the endogenous heavy chain and light chain, immunoglobulin expression.

EXAMPLE IX

This example describes an alternative method for the cloning and microinjection of an enzyme/heavy chain immunoglobulin transgene into a murine zygote.

Nuclei are isolated from mouse liver and embedded in a low melt agarose and lysed with EDTA and proteinase K releasing the high molecular weight DNA. This high molecular weight DNA is then subjected to restriction enzyme digestion with restriction enzymes which cut to yield large fragments i.e., not1 etc.

This high molecular weight fragmented DNA is then subjected to pulsed field gel electrophoresis and fragments analyzed for the combination of the mouse VH, D, JH and Mu heavy chain. These fragments are pooled and cloned into a YAC vector containing neo resistance marker. YAC clones are analyzed and those with the desired mouse heavy chain sequences of the VH, D JH and Mu heavy chain used in the further cloning series.

The VH genes from the selected YAC clone are subcloned into a plasmid vector and subjected to recloning resulting in the replacement of the VH gene with the enzyme portion of interest as described in example 1 to yield vector pVH5E. The JH region is also subcloned into a plasmid vector and subjected to the insertion of the 3' enzyme portion as described in example 2 to yield vector pJH3E.

Vector pVH5E is then subcloned with the modified VH gene containing the 5' portion of the enzyme of interest in to half a YAC vector which includes a yeast selectable marker HIS3 not present in the original YAC vector, a centromere (CEN) and a single telomere (TEL). The modified JH region subclone containing the 3' portion of the enzyme of interest from pJH3E is also subcloned into half a YAC vector which includes a yeast selectable marker LEU2 not present in the original YAC vector, and a single TEL. The half YAC vector with the modified VH gene is linearized and used to transform a yeast strain which carries the desired mouse heavy chain sequences of the VH, D JH and Mu heavy chain. Selection for the histidine prototrophy gives rise to yeast colonies that have undergone homologous recombination. The half YAC vector containing the enzyme modified JH region containing the 3' portion of the enzyme of interest is then linearized and used to transform the yeast strain generated in the previous step. Selection for leucine-prototropy results in a yeast strain containing the whole enzyme/immunoglobulin loci. Preferably, both selection steps can be carried out together. This YAC is isolated and microinjected into ES cell and the cell subjected to neo selection using G418. The resulting cell line LYS35YAC is then used to generate a chimeric mouse as described above in example V. The resulting chimeric mouse is then subjected to breeding in order to generate mice producing the enzyme antibody chimeric molecule with out the production of native antibodies. Examples 6 and 7 describe breeding protocols to remove the endogenous heavy chain and light chain, immunoglobulin expression.

EXAMPLE X

Production of enzyme diversity using the transgenic mice produced in examples 5, 6, 7, 8 and 9. Specific examples of immunization to generate novel activities are given later in examples 11, 12 and 13 following.

Immunization of the mice carrying the integrated enzyme/immunoglobulin DNA are immunized with injections of an antigen in adjuvant. These antigens can be transition state analogues or substrates or products or combinations in a single immunogen. These various immunogens can be used alone or in sequential combinations which are aimed at focusing the development of the enzyme diversity stimulated by the immunization protocol. The mice are boosted with antigen 14 days after the primary immunization. Typically this is also followed by immunizations at days 34 and 50. The response of the mice is followed with bleeds done on the immunized animals to test the specific activity of the enzyme responses against the substrate of interest. The mouse blood is subjected to a purification step based on the Mu heavy chain sequence at the COOH terminal of the recombined enzymes or the Kappa light chain depending on the specific transgenic mouse used in the immunization. Typically this purification would make use of anti mouse immunoglobulin specific antibodies on beads or other solid phase to carry out a rapid and effective purification.

The mice with the highest desired enzyme activity are sacrificed and the spleens removed for generation of the hybridomas secreting the desired enzyme activity.

Myeloma cells are used as the fusion partner to generate the hybridomas following standard methods. One day before the fusion, the cells are split into fresh medium containing 10% fetal calf serum at a concentration of $5 \times 10^5$ cells/ml. On the morning of the fusion the cells are diluted with an equal volume of medium supplemented with 20% fetal calf serum and 2X OPI (3 mg/ml oxaloacetate, 0.1 mg/ml sodium pyruvate and 0.4 IU/ml insulin) solution.

After sacrificing the mouse, the spleen is aseptically removed, and placed in a dish with culture medium. The cells are teased apart until the spleen is torn into fine pieces and most cells have been removed.

The cells are washed in fresh sterile medium, and the clumps allowed to settle out. The splenocytes are further washed twice by centrifugation in medium without serum. During the second wash, the myeloma cells are also washed in a separate tube. After the final wash the two cell pellets are combined, and centrifuged once together. A solution of 50% polyethylene glycol (PEG) is slowly added to the cell pellet while the cells are resuspended, for a total of two minutes. 10 ml of prewarmed medium is added to the cell solution, mixing slowly for 3 minutes. The cells are centrifuged and the supernatant removed. The cells are resuspended in 10 ml of medium supplemented with 20% fetal calf serum, 1X OPI solution and IX AH solution (58 $\mu$M azaserine, 0.1 mM hypoxanthine) The fused cells are aliquoted into 96-well plates, and cultured at 37° C. or one week. Supernatant is aseptically taken from each well, and put into pools. These pools are tested for enzyme activity against the substrate. Positive pools are further tested for individual wells. When a positive well has been identified, the cells are transferred from the 96-well plate to 0.5 ml of medium supplemented with 20% fetal calf serum, 1x OPI, and 1X AH in a 24-well plate. When that culture becomes dense, the cells are expanded into 5 ml, and then into 10 ml. At this stage the cells are sub-cloned so that a single enzyme/antibody producing cell is in the culture. These culture can form the basis for the production of the novel enzyme activity or the source of genetic information for the development of alternative expression and production systems for the enzyme activity using methods known to the art.

EXAMPLE XI

Generation of increased lysozyme activity and increase sequence diversity.

In this example the mice transgenic for the lysozyme/antibody fusion are stimulated with the natural substrate 'NAG NAM NAG NAM NAG NAM' for the enzyme coupled to KLH. Also the natural inhibitor NAG-lactone coupled to KLH is used as an immunogen. This formed the basis of the test system to see the stimulation of the lysozyme gene recombination and the recovery of active lysozyme.

The transgenic mice are immunized with immunogens described above as in Example 10. The active hybridomas are then subjected to PCR amplification of the lysozyme gene followed by sequencing following standard methods (Clontech Palo Alto Calif.). The lysozyme genes from the stimulated mice are found to exhibit a significant level of sequence variability demonstrating the ability of the system to generate enzyme diversity by directed stimulation.

EXAMPLE XII

Generation of diversity in the ribonuclease immunoglobulin producing transgenic mice.

In this example the ribonuclease/immunoglobulin transgenic mice are stimulated with both the natural substrate RNA and the transition substrate uridine-vanadate coupled to KLH after periodate oxidation of the cis diols in the ribose ring followed by formation of a shiffs base with the amino groups of KLH and reduction with sodium borohydride. The chimeric mice are immunized following the general protocols outlined above.

The mice are screened for increasing levels of the chimeric ribonuclease antibody activity after selective isolation of the antibody using anti antibody reagents on beads. This is found to be important due to the endogenous levels of ribonuclease found in serum.

The hybridomas isolated from these immunizations are studied both for enzyme activity and sequences of the ribonuclease. Significant differences are found in the sequences and specific activities of the clones of the ribonuclease/antibody chimeric molecules.

EXAMPLE XIII

Generation of a novel lysozyme activity based on transition state immunization.

In this example the immunogen used to stimulate the generation of the enzyme diversity is based on the amidine transition state analog previously described (WO 93/02703 incorporated by reference). Other alternatives to this transition state are known for example NAG-lactone, 1-aminogalactoside and galactal. The amidine hapten mimics the transition state for the hydrolysis of glycosidic bonds and represent a good core structure of an immunogen to stimulate the development of the lysozyme repertoire. The specific amidine is prepared to match the substrate galactose to allow the generation and selection of a galactosidase activity from the lysozyme/antibody producing mice. These immunogens are typically generated as a series with the R group being a number of various choices. In this case we focused on the use of ribose and deoxyribose coupled to the protein carrier. This amidine immunogen is coupled to the carrier protein typically keyhole limpet hemocyanine for best results. The immunization schedule is carried out as illustrated the general protocol of Example 10 above. The serum from the immunized animals is tested during the immunization using a chemiluminescent galactosidase substrate (Tropix Cambridge Mass.). The animals showing the greatest activity are used for the fusion with the hybridoma line as described above.

One skilled in the art would realize that various combinations of the above identified techniques may be employed to practice the claimed invention.

We claim:

1. A method for generating catalytic antibodies comprising:
   (a) isolating a sequence of a functional catalytic unit from an enzyme;
   (b) inserting said sequence into a germline of an animal such that said sequence undergoes antibody variable region diversification; and
   (c) identifying the generated antibodies with desired enzymatic activity.

2. A method as in claim 1 wherein said sequence is inserted in a yeast artificial chromosome.

3. A method as in claim 1 wherein said functional catalytic unit is a complete enzyme or a portion of a complete enzyme.

4. A method as in claim 1 wherein said functional catalytic unit is an inactivated enzyme.

5. A method as in claim 1 wherein said sequence is transgenically inserted into a germline of an animal and the endogenous antibody germline sequence is knocked-out or removed.

6. A method as in claim 1 wherein said identifying of the generated antibodies is a process selected from the group consisting of screening, selecting, and isolating.

7. A method as in claim 1 wherein said sequence is of human origin.

8. A method as in claim 1 wherein said sequence and said generated antibodies are of human origin.

9. The product of the process of claim 1.

10. A method for generating catalytic antibodies comprising:
    (a) isolating a sequence of a functional catalytic unit from an enzyme;
    (b) inserting said sequence into a germline of an animal such that said sequence undergoes antibody variable region diversification;
    (c) immunizing said animal with an immunogen; and
    (d) identifying the generated antibodies with desired enzymatic activity.

11. A method as in claim 10 wherein said sequence is inserted in a yeast artificial chromosone.

12. A method as in claim 10 wherein said functional catalytic unit is a complete enzyme or a portion of a complete enzyme.

13. A method as in claim 10 wherein said functional catalytic unit is an inactivated enzyme.

14. A method as in claim 10 wherein said sequence is transgenically inserted into a germline of an animal and the endogenous antibody germline sequence is knocked-out or removed.

15. A method as in claim 10 wherein said sequence is of human origin.

16. A method as in claim 10 wherein said sequence and said generated antibodies are of human origin.

17. A method as in claim 10 wherein said immunogen is selected from the group consisting of transition state analog, transition state analog attached to a substrate of interest at the site of desired catalytic action, and transition state analog attached to an analog of the substrate of interest.

18. A method as in claim 10 wherein said immunogen is selected from the group consisting of an enzyme inhibitor, an enzyme inhibitor attached to a substrate of interest at the site of desired catalytic action, and an enzyme inhibitor attached to an analog of the substrate of interest.

19. A method as in claim 10 wherein said immunogen is selected from the group consisting of a suicide substrate inhibitor, a suicide substrate inhibitor attached to a substrate of interest at the site of desired catalytic action, and a suicide substrate inhibitor attached to an analog of the substrate of interest.

20. A method as in claim 10 wherein said identifying of the generated antibodies is a process selected from the group consisting of screening, selecting and isolating.

21. The product of the process of claim 10.

22. A method for generating chimeric antibodies comprising:
   a) isolating a sequence of a functional catalytic unit from an enzyme;
   (b) inserting said sequence into a germline of an animal such that said sequence undergoes antibody variable region diversification; and
   (c) selecting the generated antibodies with the desired enzymatic activity.

23. A method as in claim 22 wherein said sequence is inserted in a yeast artificial chromosone.

24. A method as in claim 22 wherein said functional catalytic unit is a complete enzyme or a portion of a complete enzyme.

25. A method as in claim 22 wherein said functional catalytic unit is an inactivated enzyme.

26. A method as in claim 22 wherein said sequence is transgenically inserted into a germline of an animal and the endogenous antibody germline is knocked-out or removed.

27. A method as in claim 22 wherein said selecting of the generated antibodies is a process selected from the group consisting of screening, selecting and isolating.

28. A method as in claim 22 wherein said sequence is of human origin.

29. A method as in claim 22 wherein said sequence and said generated antibodies are of human origin.

30. The product of the process of claim 22.

31. A method for generating chimeric antibodies comprising:
   a) isolating a sequence of a functional catalytic unit from an enzyme;
   (b) inserting said sequence into a germline of an animal such that said sequence undergoes antibody variable region diversification;
   (c) immunizing said animal; and
   (d) selecting the generated antibodies with the desired enzymatic activity.

32. A method as in claim 31 wherein said sequence is inserted in a yeast artificial chromosome.

33. A method as in claim 31 wherein multiple different functional catalytic units or components thereof are integrated into the germline of an animal.

34. A method as in claim 33 wherein said functional catalytic units or components thereof are separated by immunoglobulin variable region intronic sequences.

35. A method as in claim 31 further comprising a process repeated iteratively where a sequence encoding the product of one iteration is the sequence integrated into a germline of an animal in the next iteration.

36. A method as in claim 31 wherein said sequence when expressed is fused to the amino terminus of an immunoglobulin chain.

37. A method as in claim 36 wherein said immunoglobulin chain is lacking a variable region.

38. A method as in claim 31 wherein said functional catalytic unit is a complete enzyme or a portion of a complete enzyme.

39. A method as in claim 31 wherein said functional catalytic unit is an inactivated enzyme.

40. A method as in claim 31 wherein said sequence is transgenically inserted into a germline of an animal and the endogenous antibody germline sequence is knocked-out or removed.

41. A method as in claim 31 wherein said selecting of the generated antibodies is a process selected from the group consisting of screening, selecting, and isolating.

42. A method as in claim 31 wherein said sequence is of human origin.

43. A method as in claim 31 wherein said sequence and said generated antibodies are of human origin.

44. The product of the process of claim 31.

45. A method for generating catalytic antibodies comprising:
   (a) isolating a sequence of a functional catalytic unit from an enzyme;
   (b) inserting said sequence into an antibody gene locus of an animal; and
   (c) identifying the generated antibodies with desired enzymatic activity.

46. A method for generating catalytic antibodies comprising:
   (a) isolating a sequence of a functional catalytic unit from an enzyme;
   (b) inserting said sequence into an antibody gene locus of an animal;
   (c) immunizing said animal with an immunogen; and
   (d) identifying the generated antibodies with desired enzymatic activity.

47. A method for generating chimeric antibodies comprising:
   (a) isolating a sequence of a functional catalytic unit from an enzyme;
   (b) inserting said sequence into an antibody gene locus of an animal; and
   (c) selecting the generated antibodies with desired enzymatic activity.

48. A method for generating chimeric antibodies comprising:
   (a) isolating a sequence of a functional catalytic unit from an enzyme;
   (b) inserting said sequence into an antibody gene locus of an animal;
   (c) immunizing said animal; and
   (d) selecting the generated antibodies with desired enzymatic activity.

* * * * *